(12) United States Patent
Petrich et al.

(10) Patent No.: US 9,326,718 B2
(45) Date of Patent: May 3, 2016

(54) BLOOD GLUCOSE MEASUREMENT FOR SMALL BLOOD VOLUME

(75) Inventors: Wolfgang Petrich, Bad Schoenborn (DE); Christian Vrancic, Mannheim (DE); Daniel Wong, Sunnyvale, CA (US); Paul Patel, Sunnyvale, CA (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 363 days.

(21) Appl. No.: 12/845,512

(22) Filed: Jul. 28, 2010

(65) Prior Publication Data

US 2011/0125059 A1    May 26, 2011

Related U.S. Application Data

(63) Continuation of application No. PCT/EP2009/050640, filed on Jan. 21, 2009.

(51) Int. Cl.
*A61B 5/157* (2006.01)
*B65D 81/00* (2006.01)
*A61B 5/15* (2006.01)
*A61B 5/145* (2006.01)

(52) U.S. Cl.
CPC ............ *A61B 5/157* (2013.01); *A61B 5/1411* (2013.01); *A61B 5/14532* (2013.01)

(58) Field of Classification Search
CPC ............ A61B 5/1411; A61B 5/14532; A61B 5/15186; A61B 5/150022; A61B 5/14514
USPC ............................ 600/583, 584; 606/181, 182
See application file for complete search history.

(56) References Cited

U.S. PATENT DOCUMENTS

| | | |
|---|---|---|
| 4,314,564 A | 2/1982 | Albarda |
| 4,943,415 A | 7/1990 | Przybylowicz et al. |
| 5,100,620 A | 3/1992 | Brenneman |
| 5,443,988 A | 8/1995 | Kitajima |
| 6,312,888 B1 | 11/2001 | Wong et al. |
| 6,325,980 B1 | 12/2001 | Christner et al. |
| 6,349,229 B1 | 2/2002 | Watanabe et al. |
| 6,541,266 B2 | 4/2003 | Modzelewski et al. |
| 6,565,738 B1 | 5/2003 | Henning et al. |
| 6,847,451 B2 | 1/2005 | Pugh |

(Continued)

FOREIGN PATENT DOCUMENTS

| | | |
|---|---|---|
| CN | 1407327 A | 4/2003 |
| CN | 1456890 A | 11/2003 |

(Continued)

OTHER PUBLICATIONS

Hoenes, J., Mueller, P., Surridge, N., "The Technology Behind Glucose Meters: Test Strips", Diabetes Technology & Therapeutics, vol. 10, Supp 1, 2008, S10-S27.

(Continued)

*Primary Examiner* — Adam J Eiseman
(74) *Attorney, Agent, or Firm* — Roche Diabetes Care, Inc.

(57) ABSTRACT

A system is proposed for detection of at least one analyte in a body fluid, in particular for detection of blood glucose. The system is designed to generate a sample of the body fluid and to transfer at least some of the sample to at least one test element, in particular a test panel. The system is designed such that a time period between the generation of the sample and the application to the test element is less than 1 second, preferably less than 500 ms.

15 Claims, 4 Drawing Sheets

(56) References Cited

U.S. PATENT DOCUMENTS

| | | | |
|---|---|---|---|
| 6,878,262 B2 | 4/2005 | Taniike et al. | |
| 6,918,874 B1* | 7/2005 | Hatch et al. | 600/365 |
| 7,154,593 B2 | 12/2006 | Eisenmann et al. | |
| 7,252,804 B2 | 8/2007 | Miyashita et al. | |
| 2002/0168290 A1 | 11/2002 | Yuzhakov et al. | |
| 2003/0018282 A1 | 1/2003 | Effenhauser et al. | |
| 2003/0028125 A1 | 2/2003 | Yuzhakov et al. | |
| 2003/0191415 A1 | 10/2003 | Moerman et al. | |
| 2003/0212344 A1* | 11/2003 | Yuzhakov et al. | 600/583 |
| 2004/0127929 A1 | 7/2004 | Roe | |
| 2004/0158137 A1* | 8/2004 | Eppstein et al. | 600/347 |
| 2006/0100543 A1 | 5/2006 | Raney et al. | |
| 2006/0264782 A1 | 11/2006 | Holmes et al. | |
| 2006/0293611 A1 | 12/2006 | Calasso et al. | |
| 2007/0219572 A1 | 9/2007 | Deck et al. | |
| 2007/0276290 A1 | 11/2007 | Boecker et al. | |
| 2008/0056947 A1 | 3/2008 | Glauser et al. | |
| 2009/0054811 A1 | 2/2009 | Boecker | |
| 2009/0182244 A1 | 7/2009 | Hoenes | |
| 2010/0094325 A1 | 4/2010 | Konya et al. | |
| 2010/0168615 A1 | 7/2010 | Amano et al. | |
| 2010/0168617 A1 | 7/2010 | Fuerst et al. | |

FOREIGN PATENT DOCUMENTS

| | | |
|---|---|---|
| CN | 1566939 A | 1/2005 |
| CN | 1929783 A | 3/2007 |
| EP | 0359831 B1 | 3/1990 |
| EP | 0988828 B1 | 3/2000 |
| EP | 1437093 B1 | 7/2004 |
| EP | 1881322 A1 | 1/2008 |
| EP | 1887355 A1 | 2/2008 |
| EP | 1992283 A1 | 11/2008 |
| EP | 2025287 A1 | 2/2009 |
| GB | 2 325 167 A | 11/1998 |
| JP | 11-347018 | 12/1999 |
| JP | 2001-074731 | 3/2001 |
| JP | 2001-170031 | 6/2001 |
| JP | 2003-339680 | 12/2003 |
| JP | 2004-216164 | 8/2004 |
| JP | 2006-517804 | 8/2006 |
| JP | 2006-231093 | 9/2006 |
| JP | 2006-314831 | 11/2006 |
| JP | 2006119127 A | 11/2006 |
| JP | 2007-082954 | 4/2007 |
| JP | 2007-527289 | 9/2007 |
| JP | 2007-330509 | 12/2007 |
| WO | WO 98/24366 | 6/1998 |
| WO | WO 00/40150 | 7/2000 |
| WO | 0172220 A1 | 10/2001 |
| WO | WO 2004/034024 A2 | 4/2004 |
| WO | 2005084546 A2 | 9/2005 |
| WO | WO 2005/084530 | 9/2005 |
| WO | WO 2005/084530 A3 | 9/2005 |
| WO | WO 2007/091671 A1 | 8/2007 |
| WO | 2007111651 A2 | 10/2007 |
| WO | WO 2008/009585 A2 | 1/2008 |

OTHER PUBLICATIONS

Mayer, G., Koehler, J., "Micromechanical compartments for biotechnological applications: fabrication and investigation of liquid evaporation", Sensors and Actuators A 60 (1997) 202-207.

International Preliminary Report on Patentability from corresponding PCT/EP2009/050640 (German Language).

Japanese Office Action (translation-in-part) issued in Japanese Application No. 2010-543481, File No. JP-17315PCT. Dispatch No. 284850, Date of Dispatch: May 7, 2013, 13 pages.

* cited by examiner

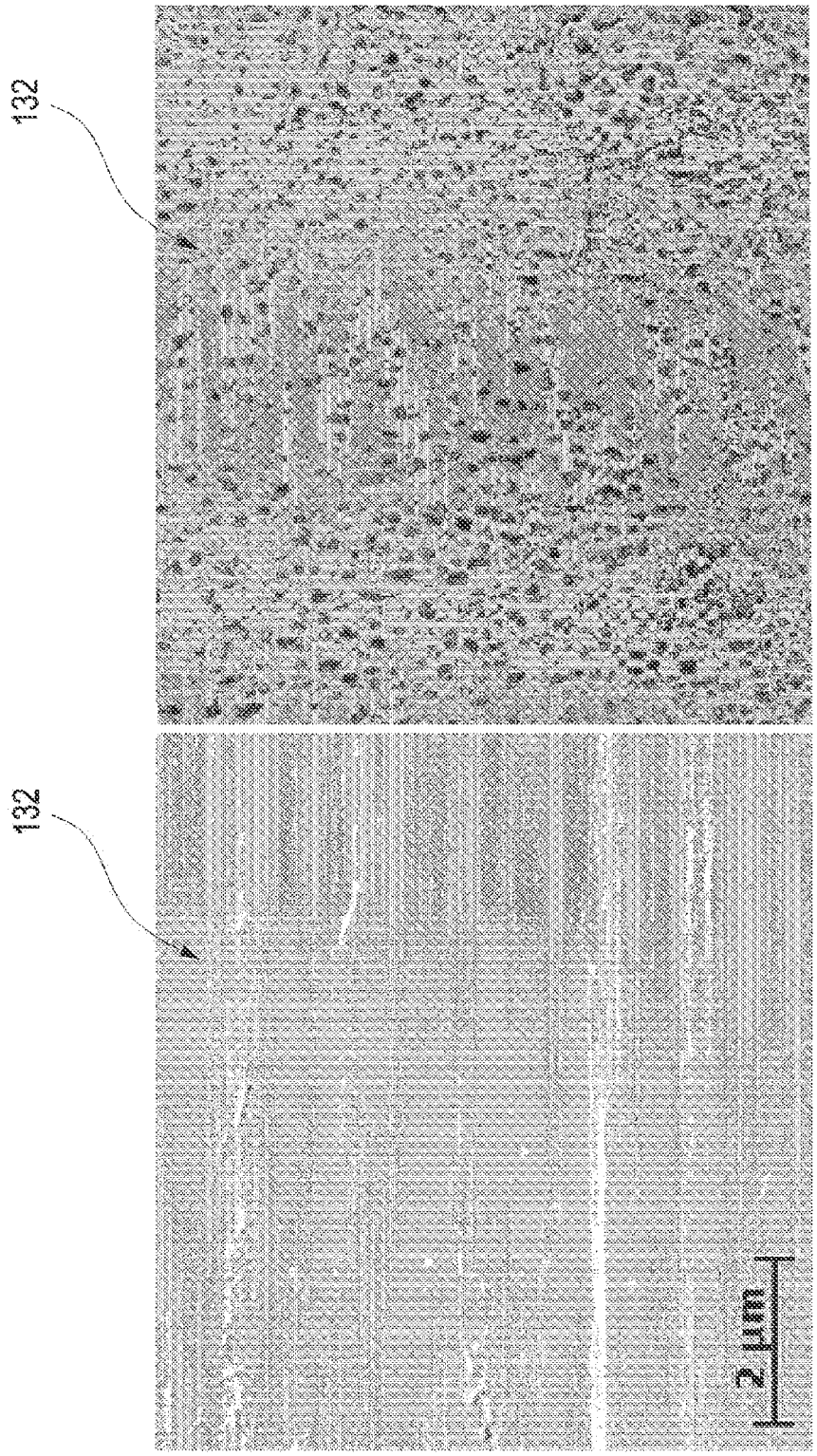

BLOOD GLUCOSE MEASUREMENT FOR SMALL BLOOD VOLUME

CLAIM OF PRIORITY

The present application is a continuation application based on and claiming priority to foreign application number PCT/EP2009/050640, filed Jan. 21, 2009, which claims the priority benefit of U.S. application Ser. No. 12/020,766, filed Jan. 28, 2008, each of which is hereby incorporated by reference in their respective entireties.

TECHNICAL FIELD OF THE INVENTION

The invention relates to a system for detection of at least one analyte in a body fluid. Such systems are used, for example, as portable detection devices or also in stationary devices, in order in particular to permit qualitative or quantitative determination of one or more analytes in body fluids such as blood or interstitial fluid. The analytes involved in particular are metabolites. The detection of blood glucose is described below in particular, without ruling out other types of analytes.

BACKGROUND

Numerous systems for detection of analytes in body fluids are known from the prior art. These systems are generally based on first generating a sample of the body fluid, for example by using at least one lancet. Then, using at least one test element, this sample is generally examined qualitatively or quantitatively for the at least one analyte that is to be detected. This can be done optically and/or electrochemically, for example. The test element can, for example, contain one or more test panels, with a test chemical that is specially designed for the detection of the at least one analyte. For example, the test chemical can undergo one or more detectable reactions or changes in the presence of the at least one analyte, which reactions or changes can, for example, be detected physically and/or chemically.

Many such systems are known from the prior art. Thus, for example, U.S. Pat. No. 7,252,804 B2, the disclosure of which is incorporated by reference herein in its entirety, describes a measuring unit for analysis of a body fluid, comprising a measuring appliance based on the use of test strips, and a lancet connected to the measuring appliance. Moreover, systems are also known in which the generation of a sample and the collection of the sample by a test element are combined. For example, EP 1 992 283 A1, the disclosure of which is incorporated by reference herein in its entirety, describes a piercing system with lancets for generating a puncture wound, and with sample-collecting devices for collecting a sample of body fluid. Following a piercing movement, a sampling movement is performed, in which the sample is collected. Similarly, EP 1 881 322 A1, the disclosure of which is incorporated by reference herein in its entirety, describes a portable measuring system for analysis of a liquid sample, which system has a moisture-proof housing with a housing interior space. The liquid sample can be applied to the at least one test element within the housing interior space.

In addition to such systems in which a sample is generated and is then transferred to the test element, systems exist in which the generation of the sample and the collection of the sample are integrated. For example, this can be done using suitable needles, which are designed wholly or partially as capillaries for collecting the liquid sample. By means of these capillaries, the liquid sample can be transferred to a test element which, for example, can be integrated into the needle or generally into a lancet device. Such lancet systems are often also referred to as "get and measure" systems. Examples of integrated lancet systems of this kind are described in WO 2005/084546 A2, the disclosure of which is incorporated by reference herein in its entirety.

Irrespective of the system used, it is a general aim of systems for detection of analytes in body fluids to considerably reduce the volume of the samples. Such a reduction is desirable for a number of reasons. First, with reduced sample volumes, it is possible to minimize the pain experienced by the patient in connection with the analysis. Moreover, large sample volumes also cause difficulties, for example in terms of an increased danger of contamination of the analysis equipment by the sample itself. A further reason for reducing the sample volumes lies in the aim of producing integrated systems. This integration requires a higher degree of functionality within the same space, such that the space available for a lancet is generally reduced, and therefore also for the sample volume. Moreover, these systems do not generally afford the possibility of actively manipulating the perforated surface of the skin ("milking") in order to increase the sample volume, such that integrated systems in most cases have to operate with smaller sample volumes.

However, as has been discovered in the context of the present invention, a difficulty in systems which operate with reduced sample volumes, for example blood volumes of less than 1 can lie in the influence of evaporation and the associated at least partial drying of the sample. However, drying of the sample, for example by evaporation of water, in turn results in an increased concentration of the substances dissolved in the liquid sample, for example glucose. In such samples, however, the raised concentrations measured are then inaccurate.

Evaporation effects of liquids have in general been widely examined and described in numerous publications in the literature. Most studies refer to free-falling water droplets or applied water droplets, not to liquids generally in depressions, which can behave fundamentally differently than free droplets. The evaporation is influenced, for example, by the air humidity and the convection in the environment of the surface of the liquid. Under normal conditions, typical evaporation rates of droplets of at least approximately 100 nl range from 0.3 to 0.6nl/s and, under constant environmental conditions, are dictated by the droplet surface area for example.

Said studies of the principles of evaporation in many cases lead to complex theoretical predictions of evaporation, which are based on knowledge of a large number of environmental factors and, parameters. However, since analysis systems for detection of analytes in body fluids in many cases have to work across a wide temperature range and air humidity range, and independently of special convection conditions, such predictions and analyses are of relatively little help in practice.

Influences exerted by drying effects are also known from the field of medical diagnostics. For example, in U.S. Pat. No. 7,252,804 B2, reference is made to the effect of this drying of blood samples in biosensors with piercing aids. Similarly, U.S. Pat. No. 6,878,262 B2, the disclosure of which is incorporated by reference herein in its entirety, refers to this effect and proposes that capillaries for blood transport be closed in order to avoid evaporation. An analogous procedure is also chosen, for example, in U.S. Pat. No. 6,565,738 B1 or in U.S. Pat. No. 6,312,888 B1, the disclosures of which are incorporated by reference herein in their entireties. In order to avoid drying out of samples, particularly by convection, it is also proposed in U.S. Pat. No. 6,325,980 B1, the disclosure of which is incorporated by reference herein in its entirety, that samples with a volume of less than 0.5 µl be covered.

Many of the known approaches thus counter the problem of evaporation by covering the capillaries, but in many cases this is almost impossible in practice or is at least difficult to achieve. Particularly in the "get and measure" systems described above, covering of the lancets, which are constructed as disposable systems, can be realized only with considerable technical effort. In many cases, therefore, evaporation from semi-open capillaries has to be considered. However, such systems with a multiplicity of interfaces can be theoretically described only with difficulty. Because of the abovementioned complex environmental conditions, particularly as regards the temperature range and/or air humidity range and the special convection conditions, it is in particular inadequate to incorporate constant correction factors into the calculation of a glucose concentration and/or of another analyte concentration. In practice, it has been shown in particular that theoretical or semi-empiric approaches to correcting the evaporation in many cases lead to unrealistically low evaporation rates and, consequently, to erroneous corrections.

Thus, an object of the present invention is to make available a system which is used for detection of at least one analyte in a body fluid and which avoids the disadvantages of known systems. The system should be inexpensive to produce but should still be able to yield improved detection results within a broad spectrum of realistic environmental conditions.

SUMMARY

This object and others that will be appreciated by a person of ordinary skill in the art have been achieved according to the embodiments of the present invention disclosed herein. In one embodiment, the present invention comprises a system for detection of an analyte in a body fluid which has the features of the independent claims. Advantageous refinements of the invention, which can be implemented singly or in combination, are set forth in the dependent claims.

The system is used for detection of an analyte in a body fluid. This fluid can, in particular, be blood and/or interstitial fluid, although other types of body fluid can also be examined alternatively or in addition. The at least one analyte, which can be detected qualitatively and/or quantitatively, can in particular be at least one metabolite. This can be blood glucose in particular. Alternatively or in addition, however, it is also possible to detect analytes such as cholesterol, lactate, coagulate, troponin, myoglobin, proBNP, C-reactive protein, CK-MB or the like. It is also possible to detect a combination of several analytes.

The proposed system is designed to generate a sample of the body fluid and to transfer it to at least one test element, in particular to a test panel. For the purpose of generating the sample, the system can in particular comprise at least one lancet for puncturing a skin part of a user. The term lancet is to be interpreted broadly and in principle includes any desired element that can generate an incision and/or puncture in the skin part. Moreover, the lancet and/or the system can comprise at least one actuator, which is designed to effect a lancet movement of the element for generating the incision and/or puncture for the purpose of generating the sample of the body fluid.

The at least one test element can comprise, for example, at least one test panel. In particular, the at least one test element, particularly the at least one test panel, can comprise at least one test chemical which, in the presence of the at least one analyte, changes at least one measurable property, for example a physically and/or chemically measurable property. For example, this can be an electrochemically measurable and/or optically measurable property, for example a color change. For this purpose, the test element, in particular the test chemical, can comprise suitable chemicals and/or chemical mixtures, for example enzymes, auxiliaries or the like, which are known in principle from the prior art and can also be used in the context of the present invention. For example, reference can be made to J. Hones et al., Diabetes Technology and Therapeutics, volume 10, supplement 1, 2008, page 10 to page 26, the disclosure of which is incorporated by reference herein in its entirety. The test elements and/or test chemicals described there can also be used in the context of the present invention.

The test element can be integrated into the at least one lancet or can be designed wholly or partially separate from the at least one lancet. If the test element is integrated into the at least one lancet, it is possible to use lancets known, for example, from known "get and measure" systems, for example in accordance with the prior art cited above. For example, one or more test panels can be arranged at the end of a closed or opened capillary or can also wholly or partially cover a capillary gap, such that the sample is transferred through the capillary gap to the test element.

To ensure the transfer of the sample, all or some of which can be transferred, to the at least one test element, several mechanisms can be provided. Thus, for example, the transfer of the sample from the site of generation to the test element can take place at least partially, or in some sections, via at least one capillary. This can in particular be a capillary that is wholly or partially integrated into a lancet. In particular, this capillary can be designed as a partially opened capillary, that is to say as a capillary in the form of an opened slit in the lancet. As has been described above, this can for example be a lancet with an integrated test element, that is to say what is called as "get and measure" lancet.

Generally, however, the expression "transfer of the sample of body fluid to the test element" is to be interpreted broadly. This expression generally means that the sample and the test element are to be moved relative to each other, that is to say are to be changed in terms of their position and/or orientation and/or extent and/or shape, such that the sample is transferred to the test element. The use of a capillary is one possibility of moving the sample itself to the test element. Alternatively or in addition, however, it is also possible to use mechanisms in which the test element is moved in order to collect the sample. For example, the system can comprise a mechanism in which the sample is initially generated on and/or in a skin part and is then transferred to the test element by a movement of the test element relative to the skin part and/or to the sample. In other words, blood for example can initially be generated in and/or on a skin part, for example of a finger, in order then to be collected from the skin surface directly via a test panel for example. The mechanism can, for example, be designed analogously to the mechanism described in EP 1 992 283 A1 or in EP 1 881 322 A1, which have been referenced hereinabove.

Proceeding from a basic system of this kind, which can be applied to all aspects of the invention described below, the invention is based on studies of the drying behavior of blood samples. These experiments were carried out in some cases on open samples, but in some cases also on capillaries, for example opened capillaries in needles. The basic result of these studies is that, as has been described above, theoretical or semi-empiric models, which are based on studies of free or applied droplets of test liquids, for example water, cannot be directly transposed to systems for detection of analytes, of the kind that are used in practice. Accordingly, three concepts are proposed, which can also be used in combination and which can be used to avoid the abovementioned problems of measurement inaccuracy caused by evaporation effects in analysis equipment and systems of the type described above. The concepts are based on the same underlying principle, namely that in conventional systems, on account of the many varied environmental conditions such as pressure, humidity, temperature, convection or similar influences in the area of the sample, corrections of the measurement results on the basis of the known analytical or semi-empiric models, for example in the context of constant correction factors or correction functions, cannot be applied unless additional measures are taken.

A first concept of the present invention is to limit the time taken for the above-described transfer of the sample of body fluid to the test element. It was discovered that, with typical and preferred sample volumes in the range below 1 μl the time between generation of the sample and application to the test element should be less than 1 second. In one embodiment, this time is less than 800 ms, and in other embodiments is less than 500 ms. In typical setups and with typical sample volumes and typical test geometries, such transfer times of less than 1 second lead to still tolerable discrepancies resulting from evaporation effects, for example discrepancies of the measured results of less than 20%, and typically of less than 5%. Therefore, according to a first aspect of the present invention, the system can be configured such that a time between generation of the sample and application to the test element is less than 1 second. In other embodiments the time is less than 500 ms. Transfer times of less than 200 ms or even of less than 100 ms may also be provided in other embodiments according to the present invention. Here, and in the text below, the transfer time is generally understood as the time between the moment an element effecting the sample transfer makes first contact with a primary sample (for example body fluid in and/or on the skin of a test subject) to the moment when the sample first makes contact with the at least one test element, in particular the at least one test chemical. A primary sample is understood here as the sample in and/or on the skin of a test subject. The transfer time can also be divided into several time segments, for example a collection time, for the actual pickup of the sample by the transfer element (for example a capillary), and the time for the actual transfer to the test element, which could also be designated as the transport time. The collection time and the transport time can also overlap since, for example, a collecting procedure does not necessarily need to have been concluded during the actual transfer.

This condition for the transfer time can be guaranteed in the system in different ways, depending on the nature of the transfer. For example, one of the above-described types of transfer can be guaranteed in the system. For example, a capillary can be used, in particular a capillary integrated into a lancet. The capillary can be closed or also at least partially opened, for example designed as an at least partially open channel with in principle any desired cross section, for example a rectangular, round or triangular cross section.

In certain embodiments, in order to achieve the above-described transfer times in systems of this kind with a capillary, such as for an opened capillary, generally and without limitation to the other above-described features, the length of the capillary is generally not more than 8 mm (length <8 mm or ≤8 mm), and in various other embodiments the length is not more than 6 mm (length <6 mm or ≤6 mm) and not more than 4 mm (length <4 mm or ≤4 mm). As capillaries, for example, it is possible to use gaps with a gap width from about 20 micrometers to about 500 micrometers. In various other embodiments the gap width is between 50 micrometers and 200 micrometers, and can be as low as 100 micrometers. Said conditions apply in particular to systems of the type described above, but also generally to other systems which are used for detection of at least one analyte in a body fluid and which are designed to generate a sample of the body fluid and to transfer at least some of it to at least one test element and in which at least one capillary is provided for the transfer of the sample.

It has been shown that a filling speed of a capillary can be dependent on the capillary length and/or capillary geometry. In particular, the filling speed of the capillary, that is to say of the capillary section relevant to the measurement, can decrease exponentially as a function of the capillary length. However, in order to ensure a short filling time, in one embodiment the capillary geometry has a ratio of the finable capillary length to the capillary diameter that is less than 100. In various other embodiments, the ratio can be less than 30, less than 20, and as low as 15 or less. Alternatively to the capillary diameter, other dimensions characterizing the width of the capillary cross section can also be used, for example, in the case of an opened capillary, such as a semi-open capillary, instead of the diameter also the length of the bottom surface plus twice the height of the capillary walls.

In order to accelerate the transfer, that is to say in order to shorten the transfer time, the at least one capillary, regardless of whether it is designed as a closed capillary or as an at least partially opened capillary, can further comprise at least one hydrophilization. This can involve one or more hydrophilic coatings, for example. Coatings with detergents can be used for example. In embodiments according to the present invention, one or more of the following materials can be used for the hydrophilization: heparin; polyacrylic acid or polyacrylic acid derivatives; chondroitin sulfate; dioctyl sodium sulfosuccinate (DSS); polysorbate; and nonionic surfactants. In this context, reference can be made, for example, to the European patent application with the application number EP 07 114 414.1, or alternatively to EP 1 887 355 A1, the disclosures of which are incorporated by reference herein in their entireties. Alternatively or in addition, however, hydrophilizing surface treatments can be carried out, for example hydrophilizing plasma treatments, for example oxygen plasma treatments or the like. In this way, the transfer of the sample can be additionally accelerated, for example since the collection time is shorter. The transfer time, which is the time between the generation of the sample on a skin part and the transfer to the test element, or to a test panel of the test element, can be composed of several segments for example. Thus, part of the transfer time can consist of a collection time and/or filling time of the capillary, followed by, for example, a transport time to the test element until the latter is brought into contact with the blood. In this way, for example, it is possible to achieve the transfer times described above.

In systems which use other transfer concepts as an alternative or addition to the use of a capillary, the stated transfer times can still be achieved. Thus, for example, the system described above can be designed to generate the sample on a skin surface, with the system being further designed to then move the test element relative to the skin surface in such a way that the test element picks up all or some of the sample. This can be done, for example, by means of the mechanism described above. The sample pickup can be configured, for example by suitable design of the mechanism, in such a way that this sample pickup takes place, in various embodiments, within a time of less than 1 second, less than 500 ms, less than 200 ms or even as low as 100 ms.

By using the stated transfer times, which lie within the stated preferred time frames, it is possible to minimize the evaporation effects and their influence on the measurement accuracy, such that the measurement accuracy lies within tolerances that are conventionally predefined in blood glucose meters for example, in the range of tolerance of 20% for example.

Alternatively or in addition to the concept of accelerating the transfer time, a second concept is further proposed in which the sample volume is deliberately influenced. As has been explained above, sample volumes of generally less than 1 µl are aimed for in modern blood glucose meters. Surprisingly, in the context of the tests described in detail below, in which it was established that the evaporation is considerably greater than would be assumed from the literature, it was nonetheless discovered that this minimizing of the sample volumes can lead to serious problems if there is no lower limit to the sample volumes. It was discovered in particular that sample volumes of 10 nl or less have such considerable evaporation effects that, in most cases, the measurement inaccuracy caused by the evaporation exceeds the range that can be tolerated at least for blood glucose meters.

Therefore, according to a further aspect of the present invention, a system of the kind described above is proposed in which the volume of the sample is less than 500 nl, and in certain embodiments can be less than 400 nl, less than 300 nl, less than 200 nl or even less than 100 nl, but still greater than 10 nl. The sample volume in an exemplary embodiment is at least 12 nl.

In the context of the present invention, the sample volume generally designates the volume of sample that is originally picked up by the system, that is to say before evaporation effects have set in. Preferably all of this sample volume is transferred to the test element, although some of it can remain in other parts of the system, for example in a capillary. Therefore, the term sample volume is to be distinguished from the total volume of the sample that is generated, for example blood on and/or in a finger pad, an ear lobe, or a skin part in the arm area. Of this total volume of the sample, only the sample volume is picked up by the system. In one embodiment, the sample volume can be detected by the system, as is explained in detail below. In the context of the present invention, the sample volume thus detected is also designated as the actual sample volume.

The sample volume can therefore lie in particular in a range of between 10 nl and 500 nl (that is to say 10 nl≤sample volume<500 nl), and in various embodiments can also be in the ranges of 10 nl<sample volume≤400 nl, 10 nl<sample volume<300 nl, 10nl<sample volume<200 nl, 10 nl<sample volume<100 nl or even in the range of 10 nl<sample volume<50 nl. The lower limit of the range is typically slightly more than 10 nl, such as at least 12 nl.

As has been indicated above, the sample can once again be transferred to the test element by one or more of the stated methods, for example. Particular mention may be made again to the transfer by means of at least one capillary, in particular by means of at least one at least partially opened capillary. Particular mention may be made again to a capillary integrated in a lancet, in particular an at least partially opened capillary. Once again, the lancet can be designed as a lancet with an integrated test element, that is to say as a "get and measure" lancet or, using the equivalent term below, as a microsampler. Alternatively or in addition, however, the system can once again also be designed with a mechanism in which the sample is first generated on a skin part and is then transferred to the test element by a movement of the test element relative to the skin part and/or to the sample. Regarding the possible configurations, reference can be made to the above description which, as has been indicated, is applicable to all of said concepts according to the invention.

Since the sample volume, as has been indicated above, plays a role in the described evaporation effects, a control of the sample volume is proposed according to the invention. This can be ensured, for example, by virtue of the fact that the system is designed to detect an actual sample volume of the sample collected by the system and/or of the sample transferred to the test element. As has been indicated above, the sample volume is to be differentiated from the total generated sample volume, for example the volume of a droplet of blood on a skin surface. The actual sample volume therefore represents an actual measured value of the sample collected by the system and/or of the sample transferred to the test element.

The detection of the analyte can then take place, for example, taking into account the actual sample volume. For example, one or more correction factors and/or other corrections, for example correction functions, can be used in order that measured values, which are generated as a result of the detection, are corrected accordingly to the actual sample volume. In this way, it is possible to at least partially compensate for evaporation effects dependent on sample volume, and for associated changes in concentration of the at least one analyte. In this way, it is possible, for example, to at least partially compensate for and/or correct increases in concentration of the sample, resulting from evaporation effects.

The actual sample volume can be detected in different ways, it being possible in principle to use any desired physical and/or chemical measuring methods for example. This detection can, for example, involve an optical detection. Thus, for example, a spatial extent of the sample can be detected optically, in particular a spatial extent on the test element and/or in a capillary. This can be done, for example, by detecting differences in contrast between the sample and the surrounding materials, which differences in contrast can also be specifically improved by suitable coloring of the system and/or of the system components coming into contact with the sample. For the optical detection, at least one optical sensor for example can be provided, for example an imaging sensor, for example a semiconductor sensor, and, if appropriate, suitable image processing. In this way, for example, the size of a spot of sample on a test panel can be detected, as a result of which conclusions can in turn be reached regarding, for example, the actual sample volume that was transferred to the test element. Similar measurement principles are known from U.S. Pat. No. 6,847,451 B2, for example, the disclosure of which is incorporated by reference herein in its entirety, in which, when using a detector array, only those fields of the array are used that have areas of a test panel sufficiently covered with sample. In contrast to this, it is possible for example, in the context of the present invention, to use similar techniques to reach quantitative conclusions regarding the actual sample volume. Alternatively or in addition, other optical measurement principles can also be used, for example diffraction measurements, transmission measurements, absorption measurements, reflection measurements, fluorescent light measurements or combinations of said and/or other optical measurements, from which conclusions regarding the actual sample volume can be drawn. For example, in a capillary and/or at another representative location of the system, it is possible to carry out absorption measurements and/or transmission measurements and/or reflection measurements from which the product of the concentration of a sample-specific substance, for example hemoglobin, and of a filling state variable, for example a filling height of a capillary, can be determined. From this, the actual sample volume can in turn be determined absolutely and/or relatively. For example, the capillary, in particular an inner surface of the capillary, can also be wholly or partially roughened, for example by an etching process. This roughening can, for example, increase a reflectance of the surface. In this way, for example, an optical contrast enhancement can be achieved, particularly in metal capillaries. The reflectance can be specifically influenced by roughening, in order to make it possible or easier, for example by absorption measurements and/or transmission measurements and/or reflection measurements, to measure a filling level and/or a volume filling in the capillary. Alternatively or in addition to an optical detection, however, other types of detections and/or sensors can also be used, for example electric sensors and/or capacitive sensors. The concept of detecting the actual sample volume can be transposed to all of the above-described transfer concepts and/or to other types of transfer concepts.

The sample volume that is collected by the system and/or transferred to the test element can be adjusted in various ways. For example, the geometries of a lancet and/or of a capillary and/or of the test element can play a role here. Thus, for example, the collected sample volume can be influenced by adjusting a capillary geometry. On the other hand, the collected sample volume can be influenced, for example, by the design of a lancet tip and/or by a puncture depth of the lancet, since, for example, generation of a larger amount of sample can lead to an increased amount of collected sample.

Particularly in connection with the detection of the actual sample volume, but also in other system configurations, the system can be designed to actively control and/or regulate the sample volume. This can be done in particular by adjusting a puncture depth of a lancet. Regulation can be provided in connection with the detection of the actual sample volume. Thus, for example, the system can be designed to detect the sample volume actually collected. Thereafter, the sample volume can be regulated, for example iteratively and/or continuously in a control process, for example by the puncture depth of a lancet and/or the duration of a puncturing procedure being influenced. This can take place in the context of a single puncturing process or also in the context of multiple puncturing. In this way, the sample volume described above can be ensured.

A third concept, which can once again also be applied in combination with one or both of the concepts described above, and which is likewise based on a knowledge of evaporation effects, is one in which the environmental conditions are specifically taken into account and/or controlled. This idea is based on the underlying concept that, in typical systems for detection of analytes, the environmental conditions can vary considerably. In particular, as has been described above, this can be the result of different geometries, air humidities, pressures, temperatures, air movements (for example convection) or similar influences.

In order to be better able to detect the influence of these parameters, which in particular can have an influence on the evaporation, it is proposed, in the context of the third concept, that a humidity, for example an absolute and/or relative air humidity, be detected during generation of the sample and/or during transfer of the sample to the test element. The detection of the analyte can then be carried out taking this humidity into account. For example, the humidity can be detected at one or more locations inside and/or outside the system, for example using one or more suitable humidity sensors. For example, the humidity can be determined at the site of generation of the sample and/or at one or more locations in the area of the sample transfer and/or at the site of the at least one test element, particularly at the site of the at least one test panel.

Alternatively, the system can be designed in such a way that the influence of variations in environmental parameters, for example air humidity, pressures, temperatures, air movements (for example convection) or similar parameters, is at least substantially eliminated, such that variations can be reduced, which in turn makes it easier to take account of the influence of these parameters, particularly of the humidity, in the detection of the at least one analyte. Accordingly, the system can be further designed such that the generation of the sample and the transfer to the test element are carried out within a substantially closed housing. A substantially closed housing is to be understood here as a housing that is generally airtight and/or moisture-proof, so as to close off an interior of the housing from an environment of the system. In this connection, reference can be made to EP 1 881 322 A1, for example, the disclosure of which is incorporated by reference herein in its entirety, and to the possible ways, set out in said document, of closing off a housing. The housing should be closed off in such a way that, at least during typical measuring times of not more than 5 to 10 seconds, for example, the environmental conditions, for example in respect of the abovementioned parameters, in the interior of the housing are practically unchanged, with the result that changes in these parameters have only a negligible influence on the evaporation rate or the change in the evaporation rate. For example, variations of not more than 5% in the evaporation rate can be tolerated.

The housing can be designed, for example, in one piece or in several pieces and can, for example, comprise a metal housing and/or a plastic housing. The housing can in particular comprise one or more openings, typically at least one closable opening. In one embodiment, the opening is designed such that a skin part, such as a skin part of a finger, can be placed wholly or partially in the opening, wherein the skin part then at least partially closes the opening. This closing of the opening by the skin part can be maintained throughout the measurement procedure, such that the above-described control of the interior of the housing from the environment is achieved. The interior of the housing can be kept as small as possible in order to keep the conditions therein as constant as possible, for example smaller than 100 ml, an in various embodiments smaller than 50 ml, and smaller than 10 ml. Alternatively or in addition, the opening can be kept very small, for example in various embodiments smaller than 100 $mm^2$, smaller than 50 $mm^2$, smaller than 20 $mm^2$, and 10 $mm^2$ or less. The sample can then be generated at or in the skin part placed in the opening. Moreover, as has been described above, the transfer of the sample to the test element also takes place inside the interior of the housing. This transfer can once again be effected, for example, by means of the above-described concepts. Thus, for example, at least one capillary can again be used, in particular a capillary at least partially integrated in a lancet. In particular, a lancet with an integrated test element can once again be used. Alternatively or in addition, however, a method can also be used in which the sample is first generated on the skin part, and at least some of the sample is then transferred to the test element by a movement of the test element relative to the skin part and/or to the sample. A mechanism can once again be provided for this purpose. Combinations of the stated transfer concepts and/or of other transfer concepts are also possible.

If at least one opening is provided, it can be closed, for example, by means of a closure mechanism while the system is not being used for measurement. For example, the opening can be closed by means of at least a slide, a flap, a flexible sealing lip or similar structures, such that the opening can be opened in order to carry out a measurement. Alternatively, however, it is also possible to provide openings which remain opened during a rest phase in which no measurement is being carried out. It is only during the measurement, when the opening is at least partially closed by the skin part, that substantially constant environmental conditions are ensured inside the interior of the housing.

As has been indicated above, in one embodiment it is proposed that a humidity be detected, in particular inside the housing, during the generation of the sample and/or the transfer of the sample to the test element. For this purpose, one or more humidity sensors can be provided which are able to detect an absolute and/or relative air humidity of the atmosphere at one or more of the abovementioned locations, for example in the interior of the housing. The system can then in particular be designed to detect the analyte taking into account the at least one humidity measurement. For example, if several humidities are measured, they can be taken into account individually or in combination, for example in the form of mean values. The humidity actually present, in particular the air humidity, which is subject to relatively small and negligible variations as a result of the described preferred encapsulation of the housing, can be taken into account using a known influence of the air humidity on an evaporation rate. Thus, for example, correction factors and/or correction functions and/or other types of corrections can be used in which, taking into account the geometries actually present in the system for example, evaporation effects at the actual air humidity and the associated increase in concentration of the sample are corrected. The corrections can be based, for example, on analytical, semi-empiric or empiric knowledge of the evaporation.

In contrast to known systems and/or theoretical approaches, a correction in the proposed system according to the third concept of the invention can be realized in a simple way. This is because at least some of the unknown influences which, in conventional systems, prevent the correction or at least make the correction difficult, are known in the proposed system and are substantially eliminated or otherwise taken into account. By means of the encapsulation by the optional housing, for example, a convection and/or a change in the convection conditions during the measurement is substantially avoided. Variations in the air humidity can also be eliminated.

Moreover, the system can also be designed to at least temporarily interrupt the detection of the analyte when a predefined minimum humidity is not attained. Thus, for example, the measurement can be discontinued and/or a warning can be generated. For example, one or more humidity thresholds can be predefined, which are compared with the actual measured value of the air humidity. For example, it is possible to establish in this way that an evaporation resulting from too low an air humidity would in fact be too great, and the associated influence of the detection of the analyte would exceed a tolerance range. In this case, for example, a warning can be output to a user to repeat the measurement at a later time and/or under different environmental conditions. Alternatively or in addition, a user can be prompted, for example, to blow or puff through an opening into the interior of the housing, in order to use the respiratory air to deliberately increase a humidity in the interior of the housing and/or at other locations.

The system can also be designed to detect at least one further parameter, particularly inside the housing, during the generation of the sample and/or during the transfer of the sample to the test element. In particular, this can be a parameter that has an influence on the evaporation or the evaporation rate of the sample and/or of constituents of the sample. For example, a pressure and/or a temperature can be detected, for example a pressure in the interior of the housing and/or a temperature of a test element and/or of the lancet and/or an air temperature, in particular inside the housing. This at least one further parameter can likewise be taken into account by certain embodiments of the present invention in the detection of the analyte in the sample, for example by suitable corrections, analogously to the above-described correction in knowledge of the air humidity.

The proposed system, which for example can be designed wholly or partially as a portable measuring appliance and/or as a stationary appliance, has many advantages over known systems. Thus, by means of the concepts described above, effects of evaporation can be influenced in a specific way (for example by detection and/or control of the sample volume) and/or at least controlled to such an extent that variations in these influences as a result of a change in environmental conditions and/or in sampling conditions can be at least substantially eliminated. For example, by means of the above-described detection of the actual volume of the sample, an evaporation rate can be assumed, for example at the same time taking account of a measured humidity in the interior of a housing. In this way, for example, a correction of the measurement can be made which, for example, takes into account the contribution of the evaporated sample. Such a correction can in particular be carried out in a technically simple way if, as has been described above, the complete procedure takes place in the interior of a housing that provides a screening of the kind described. For example, a puncturing procedure and a transfer of blood to the test element can take place entirely within the system, that is to say in the housing interior, such that a constant air humidity can be assumed during the course of the measurement.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which:

FIGS. 6A and 6B show surface images of metal capillaries without roughening and with roughening.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
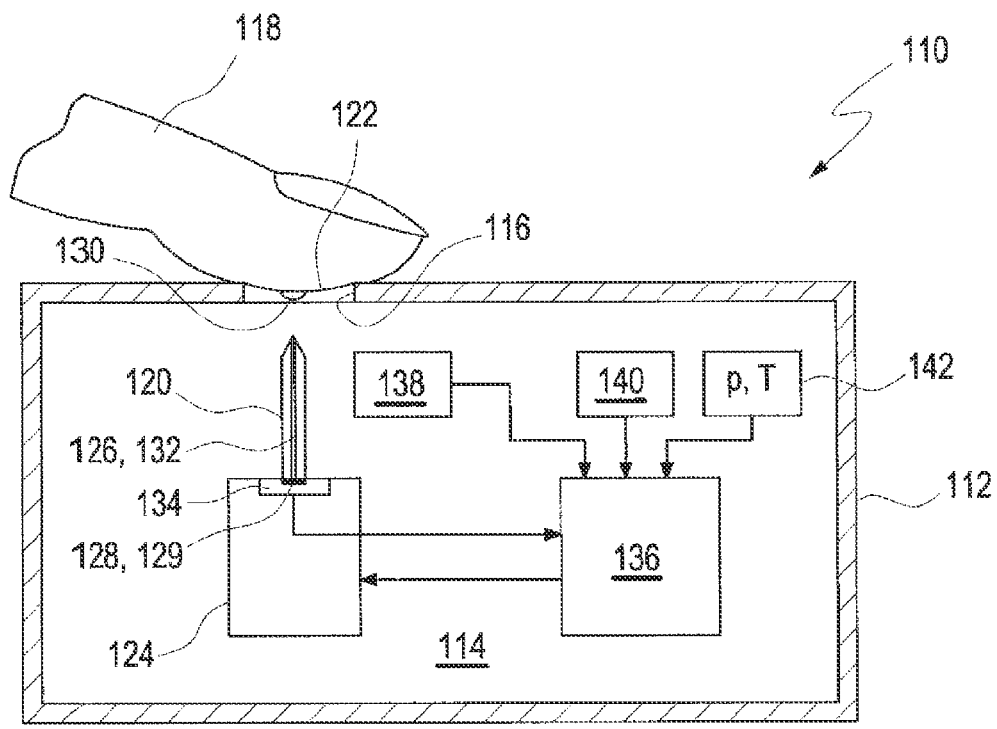
FIG. 1 shows a schematic illustrative embodiment of a system according to one embodiment of the present invention.

FIG. 1 shows a highly schematic depiction of an illustrative embodiment of a system 110 according to the invention for detection of at least one analyte in a body fluid. In the illustrative embodiment shown, the system 110 comprises a substantially moisture-proof housing 112, which has a substantially closed design. The housing 112 comprises an interior 114 which, in the illustrative embodiment shown, is temporarily accessible through an opening 116 in the housing 112 for a measurement. The opening 116 can be designed such that it can be closed, for example, by means of a slide (not shown in FIG. 1), wherein a patient or some other user can, in order to perform a measurement, open the slide using one finger 118.

A lancet 120 is arranged in the interior 114 and is designed in such a way that, when the finger 118 is placed onto the opening 116, with the finger 118 wholly or at least partially closing the opening 116, the lancet 120 punctures a skin part 122 in the area of a pad of the finger 118. An actuator 124, for example, can incite the lancet 120 to perform a puncturing movement.

In the illustrative embodiment shown, the system 110 further comprises a transfer device 126 and at least one test element 128 for detection of the analyte in a sample 130 generated on the skin part 122 by the lancet 120, in the present case a droplet of blood or interstitial fluid. In the illustrative embodiment, the transfer device 126 comprises a capillary 132, which can be formed, for example, as a gap in the lancet 120. By means of this capillary 132, the sample 130 is transferred wholly or partially to the test element 128, which in this case can be designed, for example, in one piece with the lancet 120. The lancet 120 can therefore be designed, for example, as what is called a microsampler or "get and measure" lancet.

The test element 128 can, for example, comprise a test panel 129, which is arranged at the end of the capillary 132. Moreover, a measuring device 134 can be provided, which is coupled, for example electrically and/or optically, to the test element 128, in order to detect the at least one analyte in the sample 130 after transfer to the test element 128.

It will be noted that the manner indicated in FIG. 1 for transferring the sample 130 to the test element 128 or the test panel 129 is just one of several transfer possibilities, which can also be realized in combination. For example, as has been described above, and as is known from EP 1 992 283 A1 or EP 1 881 322 A1 for example, a sample 130 can also be initially generated on the skin part 122 by means of the lancet 120, after which this sample is retrieved, for example by a suitable movement of the test element 128, from the skin part 122 and is transferred to the test element 128.

The system 110 can further comprise a control 136. This control 136 can, for example, be wholly or partially identical to the measuring device 134, but it can also be designed separately from the latter and connected thereto, as is shown in FIG. 1. The control can further be connected to the actuator 124 and can regulate the latter, for example. The control 136 can also, for example, comprise one or more data processing devices, which are able to control the entire measurement sequence of the system 110 and/or can evaluate the measurement of the at least one analyte. Alternatively or in addition, other electronic evaluation devices can be provided in the control 136. The control 136 can also be provided, for example, with one or more input and output means, for example operating elements, display elements or the like, in order to allow a user to influence the system control 110 and/or in order to output information to the user. For the design of such input and output means, reference may be made, for example, to conventional blood glucose meters.

The control 136 can also comprise, for example, one or more memories, for example volatile and/or nonvolatile memories, which can also be equipped, if appropriate, with a database system for storing measured values. The control 136 can be designed, for example, using program technology in order to execute the above-described methods in one or more of the described variants, that is to say, for example, taking evaporation effects into account and/or correcting such effects in the evaluation of the detection of the at least one analyte.

The system according to FIG. 1 further comprises a plurality of sensors. Thus, for example, an optical sensor 138 can be provided, which can detect an actual sample volume of a received sample 130 and which, for example, can be connected to the control 136 in order to transmit to the control 136 information concerning this actual sample volume. The optical sensor 138 can, for example, determine a filling level and/or a filling volume of the capillary 132, for example by means of a reflection measurement and/or by means of other optical measurement methods. The capillary 132 can, for example, be specially designed for this purpose, in particular in order to facilitate a reflection measurement. The capillary 132 can, for example, be provided with a roughened surface in order to facilitate a reflection measurement. This is illustrated by way of example in FIGS. 6A and 6B, which show surface images of metal surfaces. For example, the capillary 132 can be made of a metallic material, for example a metal sheet, for example steel. FIG. 6A shows an image of an untreated metal surface, whereas FIG. 6B shows an image of a metal surface that has been roughened by means of an etching process. For example, one capillary channel of the capillaries 132 can be wholly or partially roughened in this way, in particular in order to be able to specifically set one of the capillary channels. If information concerning the actual sample volume is obtained, for example by means of the sensor 138, the control 136 can be designed in particular to take account of this information when evaluating the measurement of the at least one analyte.

The system 110 can further comprise at least one humidity sensor 140, which can likewise be connected to the control 136 and which can measure humidity in the interior 114. The control 136 can in turn be designed to take this information on humidity into account when evaluating the measurement. One or more further sensors 142 for the measurement of further parameters can also be provided in the interior 114 and/or outside of the interior 114. For example, as is indicated in FIG. 1, one or more sensors can be provided for a pressure, a temperature or similar parameters. These sensors 142 can also be connected to the control 136, such that the evaluation of the measurement can be carried out taking into account the additional parameters.

To examine the problem of evaporation, which can have an influence on the detection of the at least one analyte in the sample 130, various studies known from the literature were assessed. Thus, when collecting blood by aspiration, for example through an open microcapillary, a partial evaporation of the blood serum can be expected even before the latter reaches the test element 128, for example the test panel 129. It will be noted that, instead of an individual test panel 129, other types of test elements 128 can also be used, for example test strips, test tapes, test disks or the like, for example test elements used in the prior art. However, the tests described below relate mainly to microcapillaries, although they can easily be transposed to other types of systems.

The described evaporation generally leads inevitably to an increase in the concentration of all the dissolved analytes. This generally causes a measurement error, which is caused early on by the sample collection on the transport path. However, by knowing the rate of evaporation that is to be expected, the error to be expected can at least be calculated. A problem here is, however, that the functionality is intended to be ensured over as wide as possible a range of temperature and function of the system 110. Therefore, a global correction, for example of 5%, is not sufficient, because the evaporation effects can vary considerably. If the aspiration of the sample 130 or the transfer always proceeds sufficiently quickly, for example being completed within 1 second, at least the time factor would not have to be taken into consideration as a variable parameter.

The evaporation, that is to say the conversion of liquid particles to the vapor phase below the boiling point, is a diffusion-limited process which has been described in different ways in the literature. The driving force of the evaporation is the concentration gradient of the vapor pressure, for example of the water vapor pressure, between the surface of the sample 130 and distant environment. The gradient becomes steeper as the ambient air becomes drier and therefore more receptive. In air at rest, this gradient as a result of the evaporation forms gradually.

By contrast, in moving air, the gradient has no opportunity to develop and form gradually. Therefore, with a draft, that is to say moving air, the concentration gradient over the liquid is maintained at its maximum, whereas, with standing air, it decreases as a result of the increasing rise in the air humidity over the liquid. Looking at the same circumstances in another way, the diffusion boundary becomes increasingly smaller and, therefore, the gradient steeper. Consequently, in the system 110 according to the invention in FIG. 1, any air movement is avoided by provision of the closed housing 112, such that both the generation of the sample 130 and also the transfer and measurement thereof by the test element 128 take place in the interior 114. In this way, the influence exerted on the evaporation rate by fluctuations caused by movements of the air is at least kept constant to the extent that, in contrast to conventional systems, it can likewise be kept constant. In this way, it is possible to avoid theoretical or semi-empiric approaches to correcting the influence of convection on the evaporation rate.

The evaporation is influenced not just by the interfering movement of air, or convection, but by a large number of parameters. Parameters within the context of the present invention are understood as all the possible influences that can have an effect on the evaporation. These can include environmental parameters, for example the air pressure, the air temperature, the air humidity, the temperature of parts of the system 110, a concentration of analytes in the sample 130 (which can exert an influence, for example, through an increase in vapor pressure) or other parameters or combinations of said and/or other parameters. In addition, system-inherent parameters are in particular the surface properties of individual parts of the system 110, for example of the capillary 132, the geometries of individual parts of the system 110, for example again of the capillary 132, or of other component parts.

Figure 2:
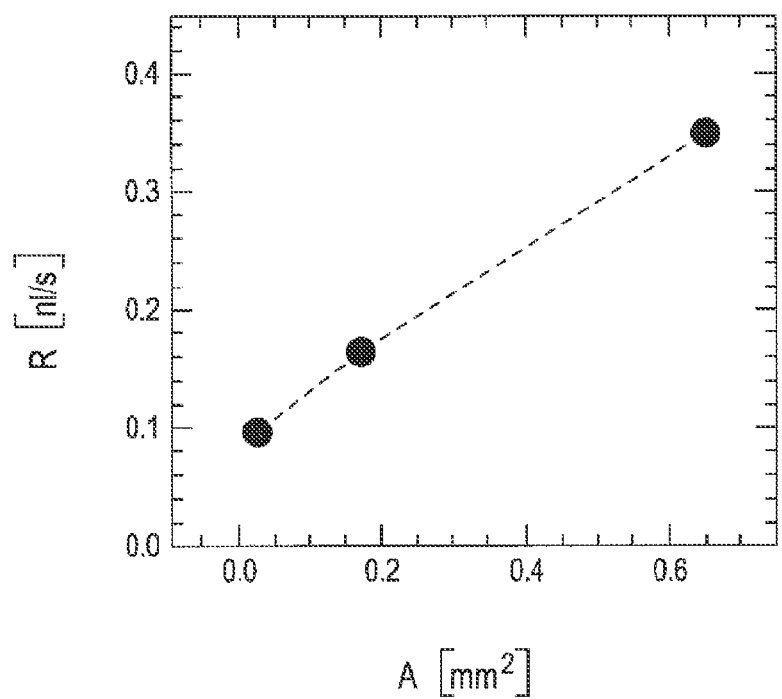
FIG. 2 shows a relationship, known from the literature, between an evaporation rate and an opening surface area of a liquid.

FIG. 2 shows a relationship, known from the literature, between an evaporation rate R, given in nl/s, and an opening surface area A, given in $mm^2$, in a pyramid-shaped, etched depression in silicon. The measurement shown is taken from Mayer et al., 1997, Sens. Actuators A, 60, 202-207. The measurements were carried out here with a sample volume of around 8 nl. The situation of these measurements is at least approximately comparable to the evaporation from semi-open capillaries, for example the capillary 132. The measurements in FIG. 2 were carried out in water, at a temperature of 22° C. and a relative air humidity of around 50%.

The measurement in FIG. 2 shows that the evaporation rate is at least approximately proportional to the surface area A. The uppermost value in FIG. 2 is from microcontainers with a surface area of 0.64 $mm^2$, which comes nearest to the surface area of open channels in flat lancets, namely around 1 $mm^2$. From said publication by Mayer et al., it is possible to extrapolate, for flat lancets with a surface area of 1 $mm^2$, evaporation rates of around 0.5 nl/s. Therefore, 100 nl of water would be evaporated in around 200 seconds.

With the volume of around 90 to 140 ηl used in the literature reference from Mayer et al., this would correspond to an initial evaporation, and therefore change in concentration, of around 0.2 to 0.3%, that is to say a value that is very low compared to the established measurement accuracy, for example of blood glucose meters. It could therefore be expected from these literature references that the problem of evaporation is irrelevant in microcapillaries.

In order to verify these predictions from the literature, experiments on evaporation from a capillary 132 were conducted. These results are shown in Table 1.

TABLE 1

Measurement results of actual evaporation rates

| Volume | Droplet | | Capillary | |
|---|---|---|---|---|
| | Water | Blood | Water | Blood |
| 150 nl | 0.6 µg/s | 0.5 µg/s | — | — |
| 50 nl | 0.5 µg/s | — | 1.0 µg/s | 1.0 µg/s |

Evaporation rates in µg/s are shown here for water and for blood. As regards the droplet, the application volume of blood was 500 nl, whereas the application volume in the capillary was 250 nl. The rates, however, were each determined at the values specified in the first column. Measurement results with an initial droplet volume of 150 nl and 50 nl are shown, which results were achieved both on droplets and also inside an opened capillary with a surface area of around 1 $mm^2$.

Figure 5:
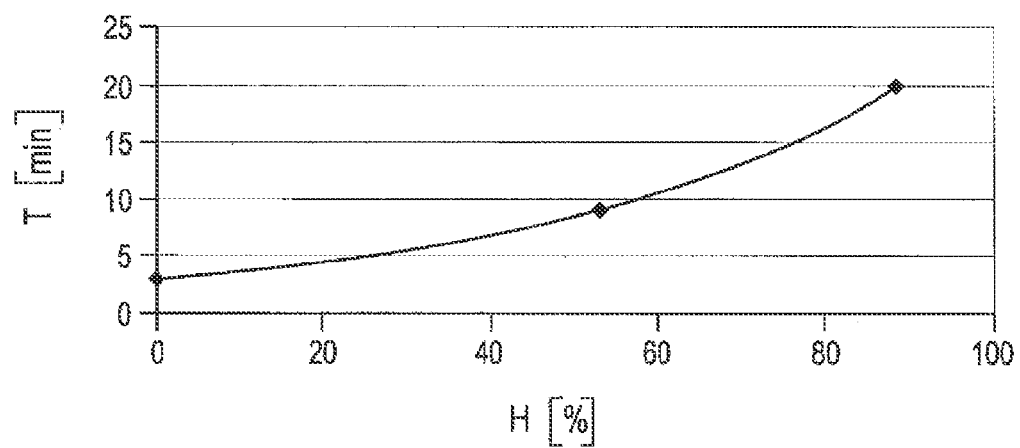
FIG. 5 shows extrapolated data of an evaporation time as a function of the relative air humidity in percent.

Surprisingly, these results show that the evaporation is much greater than was to be expected from the abovementioned literature. 1 µg corresponds to approximately 1 nl of water. The measurements were carried out at 22° C. and at a slightly lower air humidity than in the literature (45%). The slightly reduced air humidity, however, cannot be held responsible for the very great difference from the expected values, since, as tests have shown, the relative air humidity in this range, at a change of around 5%, can only influence the evaporation rate by a maximum of 20 to 30%. This is clear, for example, from the graph in FIG. 5, in which the evaporation time T in minutes for a water droplet with 0.5 mm diameter is plotted as a function of the relative air humidity H in %. This graph is also taken from Mayer et al., 1997, Sens. Actuators A, 60, 202-207.

In the measurements shown in Table 1, the convection was minimized by using an encapsulated balance. It is true that, in the measurement series shown in Table 1, a capillary with an untypical length of 8 mm was used, such that the surface area increases to around 1 $mm^2$ and, therefore, the evaporation rate, in extrapolation of FIG. 2, increases to 0.6 nl/s. It could also be argued that an applied droplet of the same volume (80 nl) has a surface area of 0.7 $mm^2$, since only a half of the droplet comes into contact with the environment. However, neither approach can in any way explain the discrepancy between the literature-based expectation (around 0.6 nl/s) and the measured values in Table 1, which are at evaporation rates of 1.0 nl/s. According to the embodiments of the invention, it is therefore proposed that the influence of the evaporation on the measurement results of the analyte determination, which influence is difficult to predict and to control, be minimized by various measures and/or be kept constant and therefore correctable and/or that this influence be eliminated by suitable control measures or corrective measures.

In one embodiment, one such measure lies in the above-described encapsulation of the system 110 by the housing 112, such as a housing 112 designed independently of the lancet 120 and/or of the actuator 124, as a result of which the evaporation by convection is minimized.

Another measure is to keep the time between the generation of the sample and the application of the sample to the test element 128 very short, such as less than 1 second.

Figure 3:
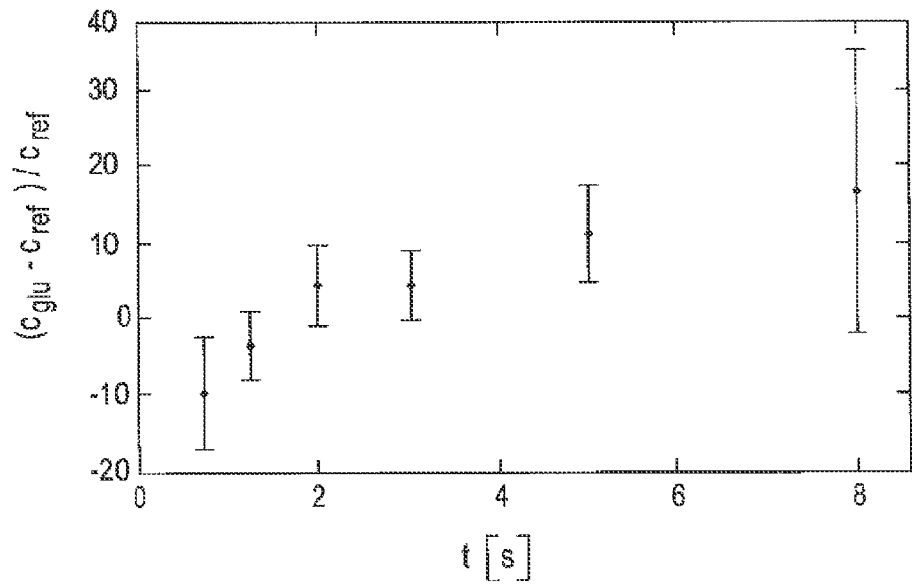
FIG. 3 shows a measurement of a relative deviation of a measured glucose concentration from the mean value as a function of the duration of the time interval between sample collection and sample application.

Thus, FIG. 3 shows relative measured deviations of a glucose concentration from a mean value of the measurement series $(c_{glu}-c_{ref})/c_{ref}$ as a function of the time t in seconds of the interval between generation of the sample and application of the sample to the test element 128, that is to say as a function of the transfer time. The tests were carried out by bringing a capillary 132 into contact with a sample 130 and then bringing the filled capillary manually into contact with a test element 128 in the form of a test strip. The test setup was in this case not encapsulated. The influence on the measured glucose concentration was thus examined.

The measurement series shown in FIG. 3 clearly illustrates a systematic change in the measured glucose value with the duration of the interval between pickup of the sample and application of the sample to the test strip. It can be seen in particular that there are significant deviations from an initial value even within 1 second. This shows that said interval between the generation of the sample and the test by the test element 128 should typically be shorter than 1 second if encapsulation of the capillary 132 is desired to be avoided.

Figure 4:
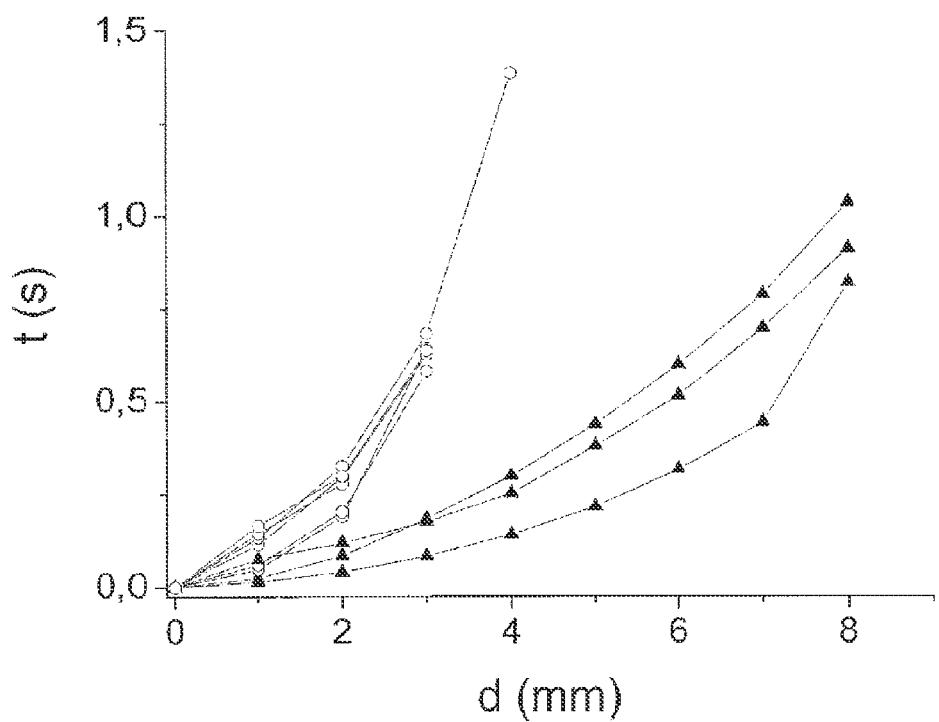
FIG. 4 shows typical filling times of differently coated capillaries.

Various possible ways of influencing this transfer time between the generation of the sample 130 and the contact with the test element 128 have already been discussed above. FIG. 4 shows an example of a possible way of influencing said transfer time, namely by influencing the surface properties of the capillary 132. A filling time t of a capillary in seconds is plotted here as part of the above-described collection time, for a capillary with a width of 120 micrometers, a depth of 80 micrometers and a length of 8 mm, as a function of a distance d in mm traveled by water within the capillary 132. Measurements were carried out on capillaries whose surfaces had been treated in various ways. In principle, for hydrophilic surface treatment, a large number of suitable methods and/or coatings or materials can be used that are also known to a person skilled in the art from other areas of technology, for example coatings with detergents. The surface treatment in FIG. 4 involves hydrophilization, for example by means of a suitable hydrophilic surface coating. In FIG. 4, the curves with the closed triangle symbols designate measurements on capillaries 132 with a hydrophilic coating, whereas the curves with the open circle symbols designate measurements on capillaries 132 without a suitable coating.

It will also be noted from the measurements in FIG. 4 that the length of the capillary 132 may also have an effect on the filling speed. Thus, for example, it will be seen from the curves with the closed triangle symbols that the partial filling time between 0 mm and 4 mm differs considerably from the partial filling time of the section between 4 mm and 8 mm. Accordingly, in embodiments of systems 110 that detect at least one analyte in a body fluid and that use at least one capillary 132 for a sample transfer, shorter capillaries 132 are typically used, irrespective of the design of the rest of the system.

Using the above-described relationship between tillable capillary length and capillary diameter, we obtain, for an embodiment of the system comprising an open capillary 132 with a width of 120 micrometers and a depth of 80 micrometers, a capillary diameter within the meaning of the above definition of 2×0.08 mm+0.120 mm=0.280 mm. For capillary lengths of 8 mm, this therefore gives a ratio of length to diameter of 29, for capillary lengths of 6 mm a ratio of 21, and for capillary lengths of 4 mm a ratio of 14. Therefore, in the context of the present invention, and with the stated capillary dimensions, various embodiments of the present invention employ capillaries 132 that have a length of not more than or even less than 8 mm, not more than or even less than 6 mm, and not more than or even less than 4 mm.

Conversely, it is possible, from these measurements of a distance d traveled within a capillary 132, and from the above-described evaporation rates, to draw conclusions concerning a minimum sample volume to be collected by the system 110 in order to keep the effects of evaporation on the measurement results tolerable.

It is thus possible to conclude, for example from the measurement results shown in FIGS. 3 and 4 and in Table 1, that more than 10 nl, such as at least 12 nl, of sample volume should be present if, at an evaporation rate of 2 nl/s and a typical capillary filling time of 100 ms and a transfer time of 200 ms, the error contributed by evaporation is to be less than the 5% that is typically still tolerable.

In addition, as has been explained with reference to FIG. 1, it is helpful if parameters that influence the evaporation and that may vary can be specifically measured by sensors and taken into consideration in the evaluation of the measurement. Thus, for example, an actual sample volume can be detected by the optical sensor 138. For example, the size of a spot of sample 130 transferred onto a test panel 129 can be detected in this way. The measurement can then be corrected to this actual sample volume, and an expected relative change in concentration caused by evaporation can thus be calculated and corrected. For example, this calculated value can be used to correct the measured value of the glucose concentration.

Other parameters can also be used additionally or alternatively for these corrections. For example, for such correction, a knowledge of the temperature, for example measured by means of the sensor 142 and/or of the air humidity, for example measured by means of the sensor 140, can additionally be included in the calculated value used for the correction. The humidity sensor 140 can, for example, comprise a commercially available hygrometer, which can be configured to save space and can be implemented inexpensively into the system 110.

Another proposal for reducing the influence of evaporation on the measurement of the analyte concentration, and one that can be implemented into a given system 110 according to the present invention in addition to or as an alternative to the possibilities described above, can involve changing the geometry of the capillaries 132. For example, an aspect ratio of these capillaries can be changed, that is to say a ratio between the width of the opening and the depth of the capillary gap. For example, the capillary can be made deeper instead of wider, that is to say have a depth of 120 μm and a width of only 80 μm instead of a depth of 80 μm and a width of 120 μm. In this way, with a constant volume, the surface area and therefore the evaporation rate are reduced.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A system for detecting at least one analyte in a body fluid, the system comprising:
   at least one test element comprising a test panel configured to detect the at least one analyte;
   at least one lancet configured to generate a body fluid sample of less than 1 µl;
   an actuator configured to incite the at least one lancet;
   at least one transfer device configured to transfer a whole or partial volume of the body fluid sample generated by the at least one lancet to the at least one test element in a transfer time of less than 1 second; and
   a measurement device configured to detect the at least one analyte, configured to detect an actual sample volume of the body fluid sample generated by the at least one lancet including a volume of the body fluid sample transferred to the at least one test element, configured to correct a measured value of the at least one analyte taking into account the actual sample volume, and configured to at least partially compensate changes in concentration to the measured value of the at least one analyte taking into account evaporation effects dependent on sample volume, wherein the measurement device comprises at least one sensor for detecting the actual sample volume.

2. The system of claim 1, wherein the transfer device comprises at least one capillary, the at least one lancet comprising at least partially a capillary, the at least one lancet comprising a partially opened capillary, or the at least one lancet comprising a wholly or partially integrated capillary and a wholly or partially integrated at least one test element.

3. The system of claim 2, wherein the transfer device is the at least one lancet comprising the wholly or partially integrated capillary and the wholly or partially integrated at least one test element.

4. The system of claim 2, wherein the transfer device comprises at least one hydrophilic coating.

5. A system for detecting at least one analyte in a body fluid, the system comprising:
   at least one test element comprising a test panel configured to detect the at least one analyte;
   at least one lancet configured to generate a body fluid sample of less than 1 µl;
   an actuator configured to incite the at least one lancet;
   at least one capillary configured to transfer a whole or partial volume of the body fluid sample generated by the at least one lancet to the at least one test element in a transfer time of less than 1 second, wherein the at least one capillary has a ratio of fillable capillary length to capillary diameter of less than 100; and
   a measurement device configured to detect the at least one analyte, configured to detect an actual sample volume of the body fluid sample generated by the at least one lancet including a volume of the body fluid sample transferred to the at least one test element, configured to correct a measured value of the at least one analyte taking into account the actual sample volume, and configured to at least partially compensate changes in concentration to the measured value of the at least one analyte taking into account evaporation effects dependent on the actual sample volume, wherein the measurement device comprises at least one sensor for detecting the actual sample volume.

6. The system of claim 5, wherein the sample the sample volume of the body fluid sample is greater than 10 nl but less than 500 nl.

7. The system of claim 6, wherein the sample volume of the body fluid sample is selected to be one of less than 300 nl, less than 200 nl, and less than 100 nl.

8. A system for detecting at least one analyte in a body fluid, the system comprising:
   at least one test element comprising a test panel configured to detect the at least one analyte;
   at least one lancet configured to generate a body fluid sample of less than 1 µl;
   an actuator configured to incite the at least one lancet;
   at least one transfer device configured to transfer a whole or partial volume of the body fluid sample generated by the at least one lancet to the at least one test element in a transfer time of less than 1 second;
   a measurement device configured to detect the at least one analyte and configured to at least partially compensate changes in concentration to a measured value of the at least one analyte taking into account sample evaporation effects on the volume of the body fluid sample, wherein the measurement device comprises at least one sensor for detecting moisture during body fluid sample generating and transferring; and
   a housing having an interior and at least one opening, wherein the at least one test element, at least one lancet, the actuator, the at least one transfer device and the measurement device are within the interior of the housing, wherein a skin part can be placed wholly or partially in the opening to at least partially close the opening, and wherein the body fluid sample is generated in the skin part placed in the at least one opening.

9. The system of claim 8, wherein the measurement device is further configured to at least temporarily interrupt the detection of the at least one analyte and/or generate a warning when a predefined minimum humidity is undershot.

10. The system of claim 8, wherein the measurement device is further configured to detect at least one further parameter within the housing during the generation of the body fluid sample and transfer to the at least one test element, and to take the at least one further parameter into account in the detection of the at least one analyte in the body fluid sample.

11. The system of claim 1, wherein the transfer device is configured such that the transfer time between the generation of the body fluid sample and the application to the at least one test element is selected to be one of less than 800 ms, less than 500 ms, less than 200 ms, and 100 ms.

12. The system of claim 8, wherein the ait least one transfer device is at least one capillary having a ratio of fillable capillary length to capillary diameter of less than 100.

13. The system of claim 1, wherein the at least one test element is connected to the at least one transfer device, and wherein the transfer time includes a collection time for pickup of the body fluid sample by the at least one transfer device and a transport time for transfer of the body fluid sample to the at least one test element.

14. The system of claim 5, wherein the at least one test element is connected to the at least one capillary, and wherein the transfer time includes a collection time for pickup of the body fluid sample by the at least one capillary and a transport time for transfer of the body fluid sample to the at least one test element.

15. The system of claim 8, wherein the at least one test element is connected to the at least one transfer device, and wherein the transfer time includes a collection time for pickup of the body fluid sample by the at least one transfer device and a transport time for transfer of the body fluid sample to the at least one test element.

* * * * *